US012083015B2

(12) United States Patent
McCarthy

(10) Patent No.: US 12,083,015 B2
(45) Date of Patent: Sep. 10, 2024

(54) ANNULOPLASTY RING SIZER

(71) Applicant: Northwestern University, Evanston, IL (US)

(72) Inventor: Patrick M. McCarthy, Evanston, IL (US)

(73) Assignee: Northwestern University, Evanston, IL (US)

( * ) Notice: Subject to any disclaimer, the term of this patent is extended or adjusted under 35 U.S.C. 154(b) by 827 days.

(21) Appl. No.: 17/251,728

(22) PCT Filed: Jun. 11, 2019

(86) PCT No.: PCT/US2019/036623

§ 371 (c)(1),
(2) Date: Dec. 11, 2020

(87) PCT Pub. No.: WO2019/241301

PCT Pub. Date: Dec. 19, 2019

(65) Prior Publication Data

US 2021/0113334 A1 Apr. 22, 2021

Related U.S. Application Data

(60) Provisional application No. 62/683,397, filed on Jun. 11, 2018.

(51) Int. Cl.

| | |
|---|---|
| ***A61F 2/24*** | (2006.01) |
| ***A61B 5/107*** | (2006.01) |
| ***A61B 90/00*** | (2016.01) |
| ***A61F 2/44*** | (2006.01) |

(52) U.S. Cl.
CPC ............ *A61F 2/2496* (2013.01); *A61B 90/06* (2016.02); *A61F 2/2445* (2013.01); *A61B 2090/061* (2016.02); *A61F 2250/0097* (2013.01)

(58) Field of Classification Search
None
See application file for complete search history.

(56) References Cited

U.S. PATENT DOCUMENTS

| | | | | |
|---|---|---|---|---|
| 6,004,329 A | | 12/1999 | Myers et al. | |
| 6,019,739 A | * | 2/2000 | Rhee | A61F 2/2496 623/2.11 |
| 6,942,694 B2 | * | 9/2005 | Liddicoat | A61F 2/2496 623/2.36 |
| 7,118,595 B2 | * | 10/2006 | Ryan | A61F 2/2409 623/2.11 |

(Continued)

FOREIGN PATENT DOCUMENTS

| | | | | |
|---|---|---|---|---|
| DE | 29911694 U1 | * | 8/1999 | A61F 2/2445 |
| WO | WO-2012135172 A2 | * | 10/2012 | A61F 2/2496 |

OTHER PUBLICATIONS

DE29911694U1 claim translation. 1999.*

(Continued)

*Primary Examiner* — Ann Schillinger
(74) *Attorney, Agent, or Firm* — Inskeep IP Group, Inc.

(57) ABSTRACT

A ring sizer including a face plate that has markings usable to provide measurements of a valve. The sizer may include a clear face plate on which the markings are provided such that the valve is visible through the face plate facilitating accurate measurements of various valve dimensions and optimal ring sizing.

9 Claims, 1 Drawing Sheet

20 10 22 26 24 32 6.1 28 38 36 10 30 60 20 38 52 54 34 54 50

(56) References Cited

U.S. PATENT DOCUMENTS 7,842,085 B2 * 11/2010 Adzich ................ A61F 2/2445 623/2.11
8,585,614 B2 * 11/2013 Ryan .................... A61F 2/2496 600/587
8,764,821 B2 * 7/2014 Carpentier ........... A61F 2/2448 623/2.36
8,915,960 B2 * 12/2014 Carpentier ........... A61F 2/2466 623/2.36
8,920,493 B2 * 12/2014 Brown ................. A61F 2/2466 623/2.11
9,101,472 B2 * 8/2015 Keidar ................. A61F 2/2466
9,687,346 B2 * 6/2017 Migliazza ............ A61F 2/2445
11,213,393 B2 * 1/2022 Winston ............... A61F 2/2496
2003/0093148 A1 * 5/2003 Bolling ................ A61F 2/2445 623/2.36
2007/0299513 A1 * 12/2007 Ryan .................... A61F 2/2448 623/2.36
2009/0093877 A1 * 4/2009 Keidar ................. A61F 2/2427 623/2.11
2009/0192600 A1 * 7/2009 Ryan .................... A61F 2/2496 623/2.11
2009/0192605 A1 * 7/2009 Gloss ................... A61F 2/2496 623/2.11
2010/0152844 A1 * 6/2010 Couetil ................ A61F 2/2448 623/2.36
2012/0253457 A1 10/2012 Winston et al.
2014/0277421 A1 * 9/2014 Conklin ............... A61F 2/2445 623/2.37

OTHER PUBLICATIONS

WIPO, U.S. International Search Authority, International Search Report and Written Opinion mailed Aug. 26, 2019 in International Patent Application No. PCT/US2019/036623, 8 pages.

* cited by examiner

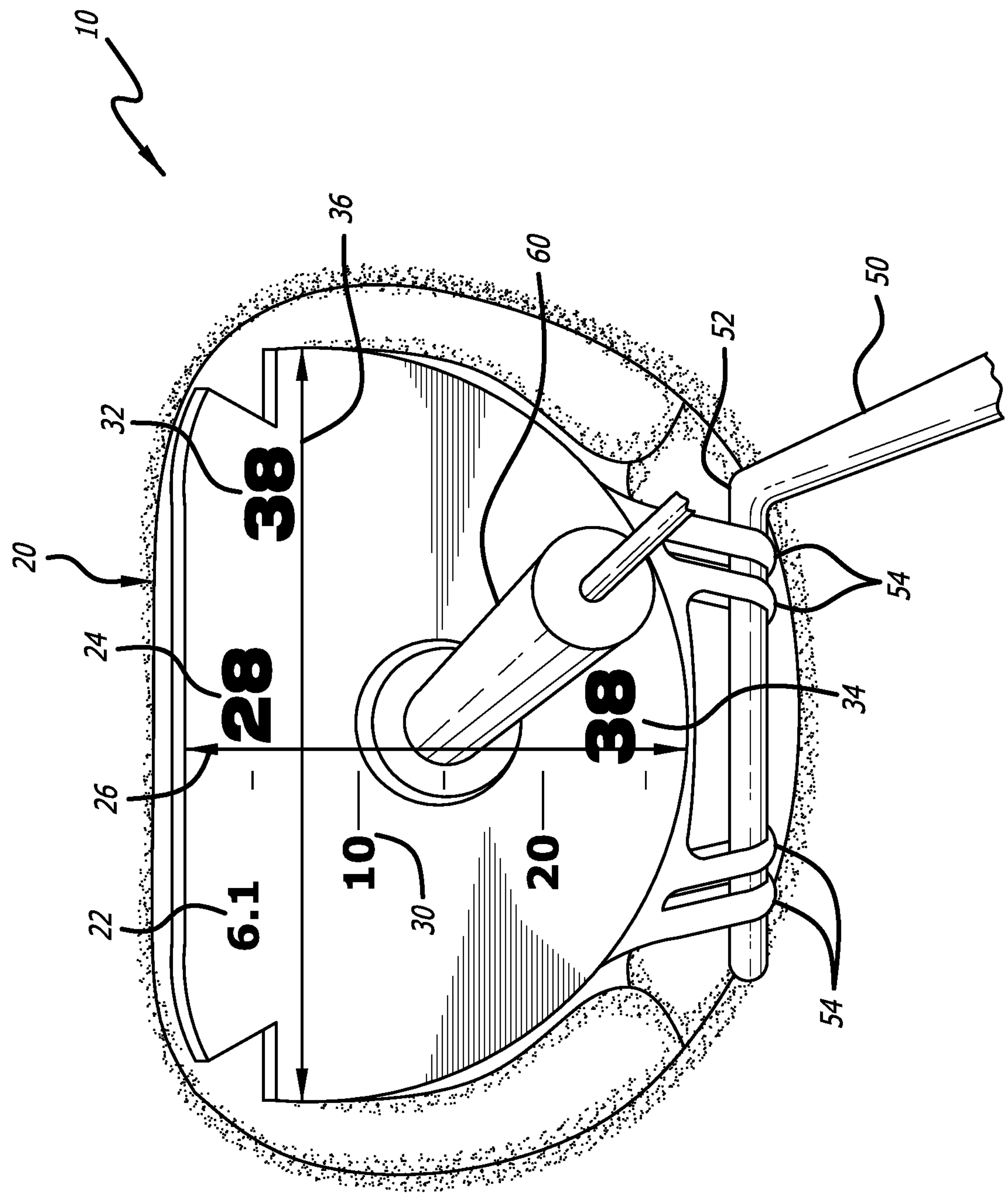
10
36
60
50
52
32
38
20
24
28
34
38
26
10
20
22
6.1
30
54
54

ANNULOPLASTY RING SIZER

RELATED APPLICATIONS

This application is the U.S. National Phase of and claims priority to International Patent Application No. PCT/US2019/036623, International Filing Date Jun. 11, 2019, entitled Annuloplasty Ring Sizer, which claims benefit of U.S. Provisional Application Ser. No. 62/683,397 filed Jun. 11, 2018 entitled Annuloplasty Ring Sizer, both of which are incorporated herein by reference in their entireties.

BACKGROUND OF THE INVENTION

Annuloplasty procedures involve remodeling a heart valve by installing a ring around the valve annulus. The ring is sized to reduce the size of the enlarged valve back to an optimal size to reestablish coaptation of the valve leaflets. These rings come in a variety of shapes and sizes. As such, a key component of a successful annuloplasty procedure is an accurate measurement of the target valve so an optimally-sized annuloplasty ring can be selected. Measurement of the native valve is accomplished with a valve sizer.

Valve sizers are typically valve-shaped rings or similar structures attached to an elongated instrument handle. The sizers are provided in sets that include numerous sizers, identified by a single number indicating the diameter across the annulus in millimeters. However, valves, such as mitral valves, are not circular, and thus generalizing them using a single measurement can result in inaccuracies, due to the variety of valve shapes. Compounding this problem is the fact that the limited information provided by existing sizers is easily misinterpreted by physicians, as valve repair is not a common procedure.

If a ring is improperly selected, implantation of the ring will lead to a "failed" repair. For example, if the ring is too large, incomplete coaptation will occur, resulting in residual valve leakage. A ring that is too small can also result in residual leakage, as well as a condition known as "systolic anterior motion," which is an obstruction of flow within the heart.

It would thus be advantageous to provide a valve sizer that provides more information to a physician, such that an optimal ring may be selected.

OBJECTS AND SUMMARY OF THE INVENTION

In one aspect of the invention, a valve sizer is provided that allows a physician to take various measurements of a valve.

Another aspect of the invention involves a valve sizer that allows a physician to measure a valve without requiring the physician to insert numerous sizers on a trial-and-error basis.

Another aspect of the invention provides a sizer made of a clear material, such as plastic, that includes a scale, allowing the physician to see through the sizer such that he or she may measure the valve.

Another aspect of the invention is a sizer that is attached to a handle made of a material, such as any of a variety of metals or plastics, that may have various lengths or have an elongatable or telescoping configuration.

Yet another aspect of the invention is a sizer having a handle that is flexible, allowing easier access to the heart.

Still another aspect of the invention is a sizer that may be used as an aid in repair or replacement of any heart valve undergoing repair or replacement.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 is a is an elevation of an embodiment of a sizer of the invention.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to FIG. 1 there is shown a sizer 10 of the invention. Sizer 10 generally includes a face plate 20 connected to a handle 50.

The face plate 20 may be formed of a variety of materials, such as metals or plastics. Advantageously, the face plate 20 could be formed of clear plastic, such that the extents of the native valve annulus may be visible through the face plate 20.

The face plate 20 includes a plurality of markings. Beginning in the upper left-hand corner of the face plate, as depicted in FIG. 1, is a first marking 22 denoting the surface area of the sizer. First marking 22 in FIG. 1 is 6.1 indicating that the surface area of the sizer is 6.1 $cm^2$.

Moving clockwise around the face plate 20, the second marking 24 denotes the anterior posterior (AP) distance. In FIG. 1, AP distance is 28 mm, as an example. As denoted by the vertical arrows 26 next to the marking 24, the AP distance is the distance from the top of the sizer to the bottom of the sizer in millimeters. To provide further clarification, the arrow 26 may be color-coordinated with the second marking 24.

Typically, AP distance is only available from charts, and is an estimation. The present invention provides actual AP measurement. In one embodiment, a calibrated scale 30 is provided next to the arrows 26 such that a physician can use the face plate 20 to obtain a measurement of the AP distance, if the sizer height does not match the valve height.

Continuing clock-wise, a third numeral marking 32 is provided, shown as the number 38 in the example of FIG. 1. This number denotes the maximum distance across the sizer 10, in millimeters. This is the sole number typically provided by sizers and is used to identify the sizer itself. For example, the sizer of FIG. 1 would typically be referred to as a "38 sizer." Keeping with this convention, a fourth marking 34 is provided (as a 38 in FIG. 1), in a larger font at the bottom of the face plate 20.

To avoid confusion, an arrow 36 may be provided under the marking 32, and optionally color-coordinated with marking 32, that shows the third marking 32 corresponds to the maximum distance across the sizer 10.

The face plate 10 is connected to a handle 50. The handle 50 may be made of various metals, plastics, or similar materials, and may be flexible or rigid, depending on the surgical approach to the valve. Additionally, the handle 50 may be telescoping or otherwise capable of being elongated.

In FIG. 1, the handle 50 is shown as having a 90 degree bend 52 that is hingedly-connected to the face plate 20 with connectors 54 for easy translation through a vessel. The angular relationship between the face plate 20 and the handle 50 may be controlled with a push rod 60. The push rod 60 may be connected to the center of the face plate 20 via a thread or other connection mechanism. The push rod 60 is offset from the handle 50 to provide leverage and is preferably located in a location where it will not interfere with the visualization of the markings.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An annuloplasty ring sizing tool comprising a face plate attached to a handle, the faceplate including a plurality of markings wherein the plurality of markings at least includes:

a number representing the surface area of the face plate;

as well as a calibrated scale usable to measure a dimension of a native valve;

a vertical line located adjacent to a linear vertical dimension marking and the calibrated scale; and a horizontal line located adjacent to a linear horizontal dimension marking, the horizontal line orthogonally intersecting the vertical line.

2. The annuloplasty ring of claim 1 wherein the face plate is hingedly attached to the handle.

3. The annuloplasty ring of claim 2 further comprising a push rod for controlling an angular relationship between the face plate and the handle.

4. The annuloplasty ring of claim 1 wherein said face plate comprises clear plastic such that native features are visible through the face plate.

5. The annuloplasty ring of claim 1 wherein the vertical line and the linear vertical dimension marking are of a same color.

6. The annuloplasty ring of claim 1 wherein the horizontal line and the linear horizontal dimension marking are of a same color.

7. The device of claim 1 wherein the linear vertical dimension marking comprises an anterior posterior length.

8. The device of claim 1 wherein the linear horizontal dimension marking comprises a maximum distance across the face plate.

9. The device of claim 1 wherein the linear vertical dimension marking includes an anterior posterior length and the vertical line and the linear vertical dimension marking are of a first color; and a maximum distance across the face plate indicated by the linear horizontal dimension marking and the horizontal line are of a second color.

* * * * *